(12) United States Patent
Gherardi et al.

(10) Patent No.: US 7,795,214 B2
(45) Date of Patent: Sep. 14, 2010

(54) VARIANTS OF THE NK1 FRAGMENT OF HEPATOCYTE GROWTH FACTOR/SCATTER FACTOR (HGF/SF) AND THEIR USE

(75) Inventors: Ermanno Gherardi, Cambridgeshire (GB); Daniel Lietha, Cambridgeshire (GB); Thomas Leon Blundell, Cambridge (GB); Dimitry Yurievich Chirgadze, Cambridgeshire (GB)

(73) Assignees: Cambridge Enterprise Limited (GB); Medical Research Council (GB)

( * ) Notice: Subject to any disclaimer, the term of this patent is extended or adjusted under 35 U.S.C. 154(b) by 680 days.

(21) Appl. No.: 11/627,761

(22) Filed: Jan. 26, 2007

(65) Prior Publication Data

US 2008/0167224 A1 Jul. 10, 2008

Related U.S. Application Data

(62) Division of application No. 10/475,616, filed as application No. PCT/GB02/01941 on Apr. 29, 2002, now Pat. No. 7,179,786.

(30) Foreign Application Priority Data

Apr. 27, 2001 (GB) ................... 0110430.6

(51) Int. Cl.
*A61K 38/16* (2006.01)
*C07K 14/00* (2006.01)
(52) U.S. Cl. ..................... 514/12; 530/350
(58) Field of Classification Search .......... None
See application file for complete search history.

(56) References Cited

U.S. PATENT DOCUMENTS 5,594,115 A 1/1997 Sharma

FOREIGN PATENT DOCUMENTS

WO 93/23541 11/1993
WO 96/40914 12/1996

OTHER PUBLICATIONS

Schwall RH et al; Heparin Induces Dimerization and Confers Proliferative Activity onto the Hepatocyte Growth Factor Antagonists NK1 and NK2, 1996, The Journal of Cell Biology, vol. 133, No. 3, p. 709-718.
A.M. Carrizosa, et al., J. Immunol. (1998) 161, p. 3307-3314.
Leitha, et al., The EMBO Journal, 20:5543-5555 (2001).
John L. Jakubczak et al., "NK1, A Natural Spice Variant of Hepatocyte Growth Factor/Scatter Factor, is A Partial Agonist in Vivo," Molecular & Cellular Biology, Mar. 1998 vol. 18, No. 3, p. 1275-1283.
Takafumi Nakamura et al., "Hepatoprotective Action of Adenovirus-Transferred HNF-3γ Gene in Acute Liver Injury Casued by $CC1_4$," Federation of European Biochemical Societies, 1999, FEBS Letters 459, p. 1-4.
Cory M. Hogaboam et al., "Novel CXCR2-Dependent Liver Regenerative Qualities of ELR-Containing CXC Chemokines," The FASEB Journal, vol. 13, Sep. 1999, p. 1565-1674.

*Primary Examiner*—Andrew D Kosar
(74) *Attorney, Agent, or Firm*—K&L Gates LLP

(57) ABSTRACT

Variants of the NK1 fragment of the polypeptide growth factor HGF/SF which act as agonists of the MET receptor and their use are disclosed. The agonists comprise at least one substitution at positions equivalent to 132, 134, 170 and 181 of full length HGF/SF (SEQ ID NO:2) and these substitutions provide variants which show scatter factor activity and induce DNA synthesis. In vivo, the variants provide protection from liver damage in a model of acute liver failure.

8 Claims, 3 Drawing Sheets

SEQUENCE LISTING

```
<160> NUMBER OF SEQ ID NOS: 2

<210> SEQ ID NO 1
<211> LENGTH: 183
<212> TYPE: PRT
<213> ORGANISM: Homo sapiens

<400> SEQUENCE: 1

Tyr Ala Glu Gly Gln Arg Lys Arg Arg Asn Thr Ile His Glu Phe Lys
 1               5                  10                  15

Lys Ser Ala Lys Thr Thr Leu Ile Lys Ile Asp Pro Ala Leu Lys Ile
            20                  25                  30

Lys Thr Lys Lys Val Asn Thr Ala Asp Gln Cys Ala Asn Arg Cys Thr
        35                  40                  45

Arg Asn Lys Gly Leu Pro Phe Thr Cys Lys Ala Phe Val Phe Asp Lys
    50                  55                  60

Ala Arg Lys Gln Cys Leu Trp Phe Pro Phe Asn Ser Met Ser Ser Gly
65                  70                  75                  80

Val Lys Lys Glu Phe Gly His Glu Phe Asp Leu Tyr Glu Asn Lys Asp
                85                  90                  95
```

-continued

```
Tyr Ile Arg Asn Cys Ile Ile Gly Lys Gly Arg Ser Tyr Lys Gly Thr
                100                 105                 110

Val Ser Ile Thr Lys Ser Gly Ile Lys Cys Gln Pro Trp Ser Ser Met
            115                 120                 125

Ile Pro His Glu His Ser Phe Leu Pro Ser Ser Tyr Arg Gly Lys Asp
        130                 135                 140

Leu Gln Glu Asn Tyr Cys Arg Asn Pro Arg Gly Glu Gly Gly Pro
145                 150                 155                 160

Trp Cys Phe Thr Ser Asn Pro Glu Val Arg Tyr Glu Val Cys Asp Ile
                165                 170                 175

Pro Gln Cys Ser Glu Val Glu
            180

<210> SEQ ID NO 2
<211> LENGTH: 728
<212> TYPE: PRT
<213> ORGANISM: Homo sapiens

<400> SEQUENCE: 2

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285
```

-continued

```
Ala Asp Asn Thr Met Asn Asp Thr Asp Val Pro Leu Glu Thr Thr Glu
    290                 295                 300
Cys Ile Gln Gly Gln Gly Glu Gly Tyr Arg Gly Thr Val Asn Thr Ile
305                 310                 315                 320
Trp Asn Gly Ile Pro Cys Gln Arg Trp Asp Ser Gln Tyr Pro His Glu
                325                 330                 335
His Asp Met Thr Pro Glu Asn Phe Lys Cys Lys Asp Leu Arg Glu Asn
            340                 345                 350
Tyr Cys Arg Asn Pro Asp Gly Ser Glu Ser Pro Trp Cys Phe Thr Thr
        355                 360                 365
Asp Pro Asn Ile Arg Val Gly Tyr Cys Ser Gln Ile Pro Asn Cys Asp
    370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
            420                 425                 430
Ser Lys Leu Asn Glu Asn Tyr Cys Arg Asn Pro Asp Asp Ala His
        435                 440                 445
Gly Pro Trp Cys Tyr Thr Gly Asn Pro Leu Ile Pro Trp Asp Tyr Cys
    450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
            500                 505                 510
Tyr Arg Asn Lys His Ile Cys Gly Gly Ser Leu Ile Lys Glu Ser Trp
        515                 520                 525
Val Leu Thr Ala Arg Gln Cys Phe Pro Ser Arg Asp Leu Lys Asp Tyr
    530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
            580                 585                 590
Phe Val Ser Thr Ile Asp Leu Pro Asn Tyr Gly Cys Thr Ile Pro Glu
        595                 600                 605
Lys Thr Ser Cys Ser Val Tyr Gly Trp Gly Tyr Thr Gly Leu Ile Asn
    610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                645                 650                 655
Ile Cys Ala Gly Ala Glu Lys Ile Gly Ser Gly Pro Cys Glu Gly Asp
            660                 665                 670
Tyr Gly Gly Pro Leu Val Cys Glu Gln His Lys Met Arg Met Val Leu
        675                 680                 685
Gly Val Ile Val Pro Gly Arg Gly Cys Ala Ile Pro Asn Arg Pro Gly
    690                 695                 700
```

```
Ile Phe Val Arg Val Ala Tyr Ala Lys Trp Ile His Lys Ile Ile
705                 710                 715                 720

Leu Thr Tyr Lys Val Pro Gln Ser
                725
```

VARIANTS OF THE NK1 FRAGMENT OF HEPATOCYTE GROWTH FACTOR/SCATTER FACTOR (HGF/SF) AND THEIR USE

FIELD OF THE INVENTION

The present invention relates to variants of the NK1 fragment of the polypeptide growth factor HGF/SF which act as agonists of the MET receptor, and to the use of NK1 and its variants in methods of treatment.

BACKGROUND TO THE INVENTION

The polypeptide growth factor hepatocyte growth factor/scatter factor (HGF/SF) (Gherardi et al., 1989; Miyazawa et al., 1989; Nakamura et al., 1989; Stoker et al., 1987) and its receptor MET, the product of the c-MET protoncogene (Bottaro et al., 1991), play essential roles in the development of epithelial organs such as the placenta and liver (Schmidt et al., 1995; Uehara et al., 1995) and in the migration of myogenic precursor cells (Bladt et al., 1995) and motor neurons (Caton et al., 2000; Ebens et al., 1996).

HGF/SF and MET are also involved in the spreading of a variety of epithelial tumours as a result of MET chromosomal rearrangements (Yu et al., 2000), somatic and/or germline mutations in the MET kinase (Schmidt et al., 1997) or, more often, over expression in tumour cells of an unrearranged and unmutated MET gene (reviewed in Jeffers et al., 1996).

HGF/SF has a unique domain structure that resembles that of the blood proteinase precursor plasminogen and consists of six domains: an N-terminal (N) domain, homologous to plasminogen activation peptide, four copies of the kringle (K) domain and a catalytically inactive serine proteinase domain (Donate et al., 1994). Two products of alternative splicing of the primary HGF/SF transcript encode NK1, a fragment containing the N and the first K domain, K1, (Cioce et al., 1996), and NK2, a fragment containing the N, K1 and second kringle, K2, domains (Chan et al., 1991; Hartmann et al., 1992; Miyazawa et al., 1991). Both NK1 (Lokker and Godowski, 1993) and NK2 (Chan et al., 1991) were initially characterized as MET antagonists, although experiments in transgenic mice have subsequently indicated that NK1 behaves in vivo as a bona fide receptor agonist (Jakubczak et al., 1998).

There is an important difference in the mechanism of receptor binding and activation by HGF/SF and NK1. HGF/SF is fully active in cells lacking heparan sulphate, while NK1 is only active in cells that display heparan sulphate or in the presence of soluble heparin (Schwall et al., 1996). Thus NK1, but not HGF/SF, resembles FGF (Rapraeger et al., 1991; Yayon et al., 1991) in terms of a requirement for heparan sulphate for receptor binding and/or activation.

Early domain deletion experiments indicated that the N domain is important for heparin binding (Mizuno et al., 1994) and site-directed mutagenesis identified residues in this domain essential for binding (Hartmann et al., 1998). Thus reverse-charge mutation of R73 and R76 decreased the affinity of HGF/SF for heparin by more than 50 fold (Hartmann et al., 1998). A role for several other positively-charged residues, such as K58, K60 and K62, was suggested from the solution structure of the N domain, as these residues are clustered in close proximity of R73 and R76 (Zhou et al., 1998), and recent NMR experiments have provided experimental support for an involvement of K60, K62, R73, R76, R78 and several other residues in heparin binding to the N domain (Zhou et al., 1999).

Despite this progress, the mechanism through which heparin and heparan sulphate confer agonistic activity to NK1 remains incompletely understood. NK1 crystallizes as a dimer in the absence of heparin (Chirgadze et al., 1999; Ultsch et al., 1998), and the features of this dimer suggested that it could represent the biologically active form of NK1 (Chirgadze et al., 1999). Nd experimental evidence, however, supports this interpretation as yet.

SEQUENCE LISTING

SEQ ID NO:1 represents amino acids 28 to 210 of the human HGF/SF protein. Residues 32-206 of HGF/SF are the wild type NK1 fragment. We have used short N- and C-terminal extensions as a matter of experimental convenience to optimise expression in yeast.

SEQ ID NO:2 is the full length HGF/SF sequence, of which residues 1-31 are the leader sequence and 32-206 the NK1 fragment.

DISCLOSURE OF THE INVENTION

Figure 1:
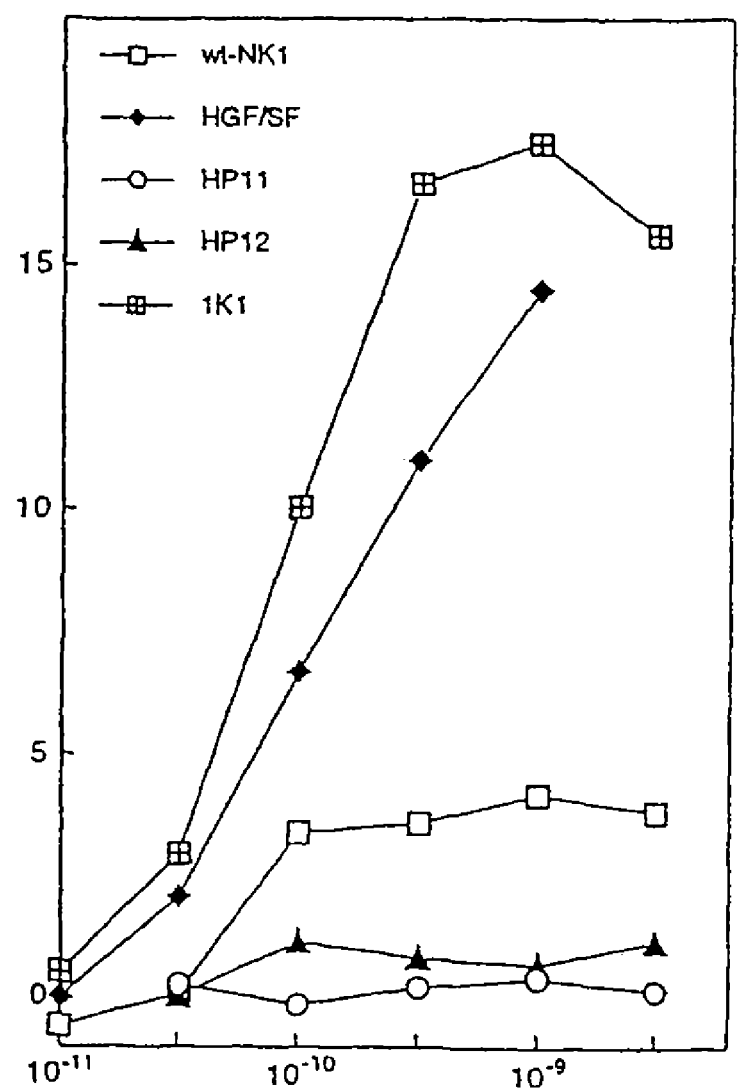
FIG. 1 shows DNA synthesis assays using MK cells. The cells were cultured to confluence in keratinocyte serum-free medium and transferred in basal medium for 24 hours before incubation with $^3$H-thymidine and HGF/SF or NK1 proteins at the concentrations (mol/L) indicated in the Figure (x-axis). DNA synthesis was measured as TCA-insoluble radioactivity; the Y axis shows $^3$H-thymidine incorporation, cpm×10$^3$/well. The HP11 mutant is inactive and the HP12 shows much reduced activity compared to wt-NK1. In contrast the 1K1 mutant is more active than wt-NK1 and full length HGF/SF.

We have determined two X-ray crystal structures of NK1-heparin complexes that define the heparin-binding site of NK1. Our analysis of these structures confirms that contacts between heparin and residues in the N-domain occur. Surprisingly though, our analysis also identifies a number of critical heparin contacts with four positively charged residues in the K1 domain. More surprisingly, we have further demonstrated that heparin binding to these positively charged residues in the K1 domain inhibits activity, and that mutagenesis of the residues provides NK1 variants with higher than wild-type activity. Such variants are useful for the production of agonists for the promotion of cell growth, particularly for angiogenesis, and the treatment of cardiovascular, hepatic, musculoskeletal and neuronal diseases.

Thus, the present invention provides a polypeptide variant of SEQ ID NO:1, said variant having the sequence of SEQ ID NO:1 apart from a substitution or deletion of least one of positions corresponding to 132, 134, 170 and 181 of HGF/SF. For ease of reference, positions of SEQ ID NO:1 are defined in relation to full length HGF/SF (SEQ ID NO:2) unless stated to the contrary. The variant is one which retains the ability to exhibit heparin-dependent dimerization in solution and to act as an agonist against the MET receptor.

The invention also provides a polypeptide which is fragment of the polypeptide variant of the invention, said fragment retaining the 132-181 region and further retaining the ability to exhibit heparin-dependent dimerization in solution and to act as an agonist against the MET receptor.

The invention further provides a composition comprising a polypeptide of the invention together with a pharmaceutically acceptable diluent or carrier.

The invention further provides a method for stimulating the growth of a cell which expresses the MET receptor, said method comprising bringing a polypeptide of the invention into contact with said cell. The cell may be in vitro or in vivo.

The invention further provides a method of treatment of a patient having a disease condition which requires stimulation of cell growth, said method comprising administering to a patient an effective amount of a polypeptide of the invention.

The invention also provides a polypeptide of the invention for use in a method of treatment of the human or animal body.

The invention further provides a polynucleotide coding for a polypeptide of the invention, as well as vectors carrying said polynucleotide, including expression vectors wherein the polynucleotide is operably linked to a promoter.

The invention further provides a host cell carrying a vector of the invention, and methods for the production of a polypeptide of the invention which comprises culturing the host cells under conditions suitable for the expression of the polynucleotide carried by the vector, and recovering the polypeptide from the cell or culture.

A major effort is underway for developing MET antagonists and agonists for therapy. MET antagonists are expected to find applications in a variety of epithelial tumours overexpressing MET, while receptor agonists may be valuable in liver regeneration, the repair of skin wounds and therapeutic angiogenesis. The structural and mutagenesis data provided by the present invention enables the generation of potent MET agonists.

DETAILED DESCRIPTION OF THE INVENTION

Polypeptides

Polypeptides of the invention are those in which one of positions 132, 134, 170 and 181 are substituted with any other amino acid. It is preferred, however, that the substitutions are those which result in a change of charge. Preferred substitutions thus include reverse charge substitutions of aspartic acid and glutamic acid.

Two or more of the positions may be substituted simultaneously. Where two substitutions are made, in a preferred aspect the two are either 132 and 134 or 170 and 181. Three substitutions may also be made or all four positions may be substituted. Where more than one position is substituted the substitutions may be the same or different.

Polypeptides of the invention may be prepared in isolated form. Isolated polypeptides of the invention will be those as defined above in isolated form, free or substantially free of material with which it is naturally associated such as other polypeptides with which it is found in the cell. The polypeptides may of course be formulated with diluents or adjuvants and still for practical purposes be isolated. The polypeptides may be glycosylated, either naturally or by systems of heterologous eukaryotic cells, or they may be (for example if produced by expression in a prokaryotic cell) unglycosylated.

A polypeptide of the invention may also be in a substantially purified form, in which case it will generally comprise the polypeptide in a preparation in which more than 90%, e.g. 95%, 98% or 99% of the polypeptide in the preparation is a polypeptide of the invention.

Polypeptides of the invention may be modified for example by the addition of histidine residues to assist their purification or by the addition of a signal sequence to promote their secretion from a cell.

SEQ ID NO: 1 represents the wild-type human form of NK1 (together with short N- and C-terminal extension). However, those of skill in the art will appreciate that in addition to the specific substitutions of the invention which result in increased activity, other positions of the wild-type molecule may be varied to a small degree without significantly affecting the overall function or structure of the polypeptide. For example, conservative substitutions can be made to many parts of proteins with no discernable impact on the structure or function of that protein. Those of skill in the art will appreciate that a small number, for example from 1-20, e.g. 2, 3, 4 or 5-10 other amino acid substitutions mainly made to NK1 and provided substitutions do not significantly alter the activity of polypeptides of the invention such variants are still regarded as NK1 polypeptides.

Fragments of the polypeptide variants of the invention which retain the region 132-181 also form a further part of the invention. Such fragments may be from 70 to 190 amino acids in size, for example from 100 to 180 in size. An example of such a fragment is provided herein as the NK1 fragment of amino acids 32-206. Another fragment is one which includes at least 70 contiguous amino acids of the Kringle 1 domain, which is found at 128-206. Preferably the fragment contains this domain in its entirety.

Methods to determine whether a polypeptide of the invention retains the ability to exhibit heparin-dependent dimerization in solution are set out in the accompanying examples. As indicated, the polypeptide may be incubated in with an equimolar concentration of heparin in a 300 mM NaCl buffer and analysed by gel filtration or western blotting.

Likewise, the ability to act as an agonist of the MET receptor may be determined in accordance with the accompanying examples. This may involve incubating the polypeptide with murine keratinocyte cells (e.g. MK cells) at a concentration of $10^{-10}$ M or higher (e.g. $10^{-10}$ to $10^{-8}$ M, and determining whether there is an increase in DNA synthesis in the cells.

A polypeptide according to the present invention may be isolated and/or purified (e.g. using an antibody) for instance after production by expression from encoding nucleic acid (for which see below). Polypeptides according to the present invention may also be generated wholly or partly by chemical synthesis, for example in a step-wise manner. The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below.

A polypeptide of the invention may be labelled with a revealing label. The revealing label may be any suitable label which allows the polypeptide to be detected. Suitable labels include radioisotopes, e.g. $^{125}I$, enzymes, antibodies, polynucleotides and linkers such as biotin. Labelled polypeptides of the invention may be used in diagnostic procedures such as immunoassays in order to determine the amount of a polypeptide of the invention in a sample.

Polypeptides and compositions thereof according to the invention may be used in methods of treatment. Such treatment will be directed to promoting the growth of cells in the human body which express the MET receptor. Such therapy will be useful for the promotion of angiogenesis and thus will be useful for the treatment of chronic skin wounds, chronic liver and kidney disease, degenerative musculoskeletelal and neuronal diseases and cardiovascular disease.

A particular use of the polypeptides of the invention is in the treatment or prevention of liver damage caused by intoxication by N-acetyl-p-aminophenol (known commercially as paracetamol or acetaminophen). We have found that administration of a polypeptide of the invention in a mouse model substantially increases survival rates of mice following administration of a lethal dose of paracetamol. Some protection is also provided by the NK1 peptide itself. Thus in this aspect of the invention, there is also provided the use of an NK1 peptide for the above-mentioned treatment.

Thus the invention provides a method of treatment or prevention of liver damage in a subject who has ingested N-acetyl-p-aminophenol, the method comprising administering to the subject an effective amount of a polypeptide of the invention or an NK1 polypeptide.

The invention also provides a polypeptide of the invention or an NK1 polypeptide for use in a method of therapy of a human or animal subject, particularly for treatment or prevention of liver damage in a subject who has ingested N-acetyl-p-aminophenol.

We have also demonstrated that the NK1 peptide as well as the 1K1 polypeptide is effective in treating acute liver failure caused by α-amanitin, which is a potent specific inhibitor of RNA polymerase II. Thus the NK1 peptide as well as the peptides of the invention as defined herein may be used generally in a method of treatment of liver disease, particularly disease conditions associated with liver failure. Such conditions include not only toxicity caused by N-acetyl-aminophenonl, but also include other drug-induced and other causes of liver failure, or disease.

Thus these peptides may be used to treat or prevent acute liver failure or disease induced by toxins, including a toxin selected from mushroom poisoning (e.g. Amanita phalloides), arsenic, carbon tetrachloride (or other chlorinated hydrocarbons), copper, ethanol, iron, methotrexate and phosphorus.

The invention may further be used to treat or prevent liver failure or disease caused by other means, including conditions selected from viral infection (such as by infection with a hepatitis virus, e.g. HAV, HBV or HCV), or other acute viral hepatitis, autoimmune chronic hepatitis, acute fatty liver of pregnancy, Budd-Chiari syndrome and veno-occlusive disease, hyperthermia, hypoxia, malignant infiltration, Reye's syndrome, sepsis, Wilson's disease and in transplant rejection.

Polypeptides may be administered in any suitable form, for example in a pharmaceutical composition such as water, saline, dextrose, glycerol, ethanol and the like. Compositions may be formulated for injection, for example for direct injection to the site of intended treatment or intravenous injection.

Suitable doses of polypeptides will ultimately be at the discretion of the physician taking account of the nature of the condition to be treated and the condition of the patient. In general, dosage ranges will be 1 µg to 1 mg per kg body weight. The polypeptides may be administered by any suitable route, e.g. by i.v. or i.p injection, or directly to the site of treatment.

By "treatment" it will be understood that this refers to any administration of a polypeptide intended to alleviate the severity of a disease being treated, to provide relief from the symptoms of the disease or to prevent or slow down the development of the disease in an individual with a disease condition or at risk of developing the disease condition.

Polynucleotides.

A polynucleotide of the invention is one which encodes a polypeptide of the invention as defined above. This includes DNA and RNA polynucleotides. A polynucleotide of the invention may be single or double stranded.

Generally, a polynucleotide according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression.

Sequences encoding all or part of the polypeptides of the invention and/or its regulatory elements can be readily prepared by the skilled person using the information and references contained herein and techniques known in the art (for example, see Sambrook, Fritsch and Maniatis, Molecular Cloning, A Laboratory Manual, Cold Spring Harbor Laboratory Press, 1989, and Ausubel et al, Short Protocols in Molecular Biology, John Wiley and Sons, 1992). These techniques include the use of site directed mutagenesis of nucleic acid encoding NK1, as described in the accompanying examples.

Vectors.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Expression Vectors.

Preferably, a polynucleotide of the invention in a vector is operably linked to a control sequence which is capable of providing for the expression of the coding sequence by the host cell, i.e. the vector is an expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage phagemid or baculoviral, cosmids, YACs, BACs, or PACs as appropriate. Vectors include gene therapy vectors, for example vectors based on adenovirus, adeno-associated virus, retrovirus (such as HIV or MLV) or alpha virus vectors.

The vectors may be provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. The vector may also be adapted to be used in vivo, for example in methods of gene therapy. Systems for cloning and expression of a polypeptide in a variety of different host cells are well known.

Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others.

Promoters and other expression regulation signals may be selected to be compatible with the host cell for which the expression vector is designed. For example, yeast promoters include S. cerevisiae GAL4 and ADH promoters, S. pombe nmt1 and adh promoter. Mammalian promoters include the metallothionein promoter which is can be included in response to heavy metals such as cadmium. Viral promoters such as the SV40 large T antigen promoter or adenovirus promoters may also be used. All these promoters are readily available in the art.

The vectors may include other sequences such as promoters or enhancers to drive the expression of the inserted nucleic acid, nucleic acid sequences so that the polypeptide is produced as a fusion and/or nucleic acid encoding secretion signals so that the polypeptide produced in the host cell is secreted from the cell.

Vectors for production of polypeptides of the invention of for use in gene therapy include vectors which carry a minigene sequence of the invention.

Vectors may be introduced into a suitable host cell as described above to provide for expression of a polypeptide of the invention. Thus, in a further aspect the invention provides a process for preparing polypeptides according to the invention which comprises cultivating a host cell carrying an expression vector as described above under conditions to provide for expression by the vector of a coding sequence encoding the polypeptides, and recovering the expressed polypeptides. Polypeptides may also be expressed in in-vitro systems, such as reticulocyte lysate.

A further embodiment of the invention provides host cells carrying the vectors for the replication and expression of polynucleotides of the invention. The cells will be chosen to be compatible with the said vector and may for example be bacterial, yeast, insect or mammalian.

The introduction of vectors into a host cell may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

A further aspect of the present invention provides a host cell containing nucleic acid as disclosed herein. The polynucleotides and vectors of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

In the accompanying examples we show that wt-NK1 behaved as a partial agonist, as expected from the prior art. It produced full dispersion of MDCK colonies and stimulation of DNA synthesis in MK cells (FIG. 1). Interestingly, maximal stimulation of DNA synthesis by wt-NK1 occurred at concentrations as low as $10^{-10}$ M, a concentration much lower than those required in other studies see for example (Schwall et al., 1996). The higher potency of NK1 observed in our studies may reflect the source (yeast vs. bacterial), and hence the activity, of the protein used.

While wt-NK1 remains less active than full length HGF/SF, remarkably the two K domain mutants exhibited biological activity much higher than wt-NK1 and equal or higher to full length HGF/SF. Our biochemical data suggest that the K domain mutations result in increased net affinity of NK1 for heparin. Thus the patch of amino acids consisting of K132, R134 and R181 acts as a negative effector of heparin binding to NK1 and reverse-charge mutations of these residues increases heparin binding probably via the main site in the N domain.

Regardless of the mechanism, we have demonstrated that substitution of two amino acids in the K domain (K132:R134 or K170:R181) is sufficient for converting NK1 into a full receptor agonist. NK1, but not HGF/SF, can be produced in yeast and is expected to exhibit favourable in vivo kinetics and tissue distribution compared to full length HGF/SF.

EXAMPLE 1

In this example the production and analysis of the biological activity of two NK1 variants of the invention is illustrated. We show that these variants undergo dimerization in a manner similar to NK1 in the presence of heparin and are rendered potent receptor agonists through mutagenesis of a cluster of positively-charged residues on the K domain.

Materials and Methods

Cloning, Mutagenesis, Expression and Purification

Cloning, expression and purification of wt-NK1 were carried out as described in (Chirgadze et al., 1999), except that final purification of NK1 by cation exchange chromatography was carried out on a Source15S column (Amersham Pharmacia Biotech). For expression of NK1 mutants, an EcoRI-NotI fragment from the wt-NK1 expression construct in pPIC9K was cloned into the pBluescript KS-vector (Stratagene) and DNA amplification reactions were carried out using complementary pairs of mutagenic oligonucleotides. The N-domain mutants were produced by DNA amplification of the relevant fragments from full length human HGF/SF cDNA which carried R73E:R76E mutations (mutant HP11) or the (K58E: K60E:K62E) mutations (mutant HP12). N domain and K domain mutants were finally cloned in the expression vector pPIC9K. Transformation and selection of P. pastoris was carried out as described previously (Chirgadze et al., 1999).

Purification of Heparin Fragments

Sodium heparin from bovine lung (Upjohn) was digested with heparinase I (Leo Pharmaceuticals) for 14 min at 37° C. in 10 mM phosphate buffer, 1.25 mM $CaCl_2$, pH 7.0. The water was evaporated, the residue dissolved in 20 g/l ammonium bicarbonate and loaded onto a Biogel P-10 (Biorad) column. Fractions containing heparin fragments of the same length (up to hexadecasaccharide) were combined and water and ammonium bicarbonate evaporated on a Rotavapor (Buechi). The heparin fragments were then dissolved in 0.1 M ammonium acetate and an aliquot was run through a G3000 SW XL (30 cm×7.8 mm) and a G2000 SW XL (30 cm×7.8 mm) GPC column on a HPLC system (Gilson) in order to assess purity and concentration. The fragments were next lyophilized and redissolved in water (3 cycles) in order to eliminate ammonium acetate.

Characterization of wt- and Mutant NK1-Heparin Complexes

This was carried out by gel filtration chromatography and cross-linking experiments. For gel filtration, wt- or mutant NK1 (0.5 mg/ml) were incubated for 2 hours in the presence or absence of equimolar concentration of 14-mer heparin in phosphate buffered saline (PBS) adjusted to 300 mM NaCl. Samples were then loaded onto an HR30 Superdex 200 column (Ammersham Pharmacia Biotech) and eluted at 0.5 ml/min.

For cross-linking, 10 μl of wt- or mutant-NK1 (0.1 mg/ml) were incubated in the absence or presence of an equimolar concentration of 14-mer heparin in PBS. After 2 hours incubation at room temperature, 1 μl of crosslinker (BS3, Pierce) was added at 100 fold molar excess, the reaction was continued for 30 minutes and then quenched with 1 μl of 1M Tris-Cl, pH 7.4. Reaction products were loaded onto 15% SDS-polyacrylamide gels and blotted onto a nitrocellulose membrane (Schleicher & Schuell). The membrane was blocked in 2% skimmed milk, incubated for 1 hour in the presence of sheep anti-HGF/SF polyclonal antibody (1W53, 1:1000), washed with PBS+0.2% Tween 20 and next incubated for 1 hour with HRP-conjugated anti-sheep immunoglobulin antibody (Dako). HRP activity was detected after 3 further washes in PBS+0.2% Tween 20 using a chemiluminescent substrate (Pierce).

MDCK Colony Scatter Assays

Scatter assays were carried out as described in (Gherardi et al., 1989; Stoker et al., 1987). Briefly, MDCK cells were plated at $1-2.5 \times 10^3$ cells/60 mm dish and cultured in 5% fetal calf serum in DMEM for 2-3 days before addition of HGF/SF or wt- or mutant NK1. After overnight incubation, plates were inspected and several colonies from each plate were photographed using a Leica DM IRB inverted microscope equipped with phase contrast optics and a Hamamatsu colour chilled 3CCD camera.

DNA Synthesis in MK Cells

The mouse keratinocyte line MK was cultured to confluence in keratinocyte SFM medium (Gibco) supplemented with 5 ng/ml EGF-53 and 50 g/ml bovine pituitary extract (BPE) in 24 well tissue culture plates (Costar). At confluence, complete medium was replaced with basal medium (no EGF and BPE) for 24 h before addition of 1 Ci/well $^3$H-thymidine in basal medium containing 1 mg/ml BSA and HGF/SF or NK1 proteins at the concentrations specified in the legend to FIG. 1. After 16 hours the cells were transferred on ice, washed with PBS and incubated in ice-cold, 5% trichloroacetic acid (TCA) for 30 min. TCA insoluble radioactivity was measured by scintillation after 2 washes with water and lysis in 0.2 M NaOH for 30 minutes at 37C.

Results

The NK1 fragment of HGF/SF (amino acids 28-210) was expressed in the methylotrophic yeast *P. pastoris* as described (Chirgadze et al., 1999) and crystallized in complex with a tetrahexameric (14-mer) heparin fragment. The heparin fragment was prepared by digestion and purification from polydisperse heparin extracted from bovine lung.

The crystallization of the protein in complex with heparin is described in GB0110430.6 of 27 Apr. 2001, from which priority is hereby claimed and the contents of which are hereby incorporated by reference, and in Lietha, D. et al.; EMBO J. 2001 Oct. 15; 20(20):5543-55, whose contents are also hereby incorporated by reference. The crystallization and analysis of the complex allowed the present inventors to identify amino acid residues in NK1 which could be altered. Having identified such residues, those of skill in the art to produce variants of the invention based on the present disclosure herein.

Briefly, two crystal types were found. The asymmetric unit of crystal type A contains two NK1 protomers, A and B, assembled into a head-to-tail dimer, as in the previously described crystal structures of NK1 (Chirgadze et al., 1999; Ultsch et al., 1998). A hepes molecule is bound to each of the K domains in the putative lysine-binding pocket, as in the 1bht structure (Ultsch et al., 1998). A heparin molecule (H) was clearly seen bound to the N domain of protomer A but the N domain of protomer B is partially disordered and poorly defined at the periphery. Thus it could not be seen whether a heparin molecule was bound. The heparin molecule bound to protomer A also makes contacts with the kringle domain of protomer A' from the neighbouring asymmetric unit of the crystals. The final refined structure contained 5 heparin sugar units: 2 glycosamines (GlcN) and 3 iduronic acids (IdoA) of the 14 present in the complex.

In contrast, the asymmetric unit of crystal type B contained an assembly of four NK1 dimers (A & B, C & D, E & F, G & H) with six bound heparin molecules. The dimers in the asymmetric unit were positioned in a circle with a pseudo-two fold axis running through the centre. The NK1 dimer arrangement was identical to that observed in crystal type A and described earlier (Chirgadze et al., 1999; Ultsch et al., 1998). Unlike the structure of crystal type A, all residues between 38 and 208 are well ordered and show clear electron density in all protomers. All N domains interact with heparin molecules. The N domains of protomers A and E share a heparin molecule as do N domains of protomers D and G. The longest heparin fragment, that could be built into electron density maps, is nine sugar units in length; it is bound to the N domain of protomer C and the K domain of protomer F. Other heparin molecules are less defined with the shortest fragment containing only five sugar units (heparin molecule N). Each K domain has a hepes molecule bound in the same binding pocket as in the structure of crystal type A. The dimers within the asymmetric unit show a good agreement with r.m.s.d. values of Cα atoms between 0.50 Å (comparing dimer consisting of protomers A and B with that consisting of protomers G and H) and 1.32 Å (comparing dimer consisting of protomers A and B with that consisting of protomer C and D). The NK1 dimers in crystal type B are also very similar to the dimer in crystal type A, with the worst r.m.s.d. of Cα atoms amounting to 1.19 Å for the dimer consisting of protomers A and B.

Heparin—K domain interactions were seen in both crystal structures and involved a cluster of positively charged residues (K132, R134, K170, R181). These residues form a patch of positive electrostatic potential lining against the negatively charged heparin chain. The functional significance of the heparin—K domain interactions was probed by mutagenesis.

Novel NK1 Mutants

Two reverse-charge N domain mutants (HP11 and HP12) and two K domain mutants (1K1 and 1K2) were generated (Table 1) and characterized for heparin binding and biological activity.

TABLE 1

| NK1 Mutant | Substitutions |
| --- | --- |
| HP11 | R73E:R76E |
| HP12 | K58E:K60E:K62E |
| 1K1 | K132E:R134E |
| 1K2 | K170E:R181E |

Cross-linking (Schwall et al., 1996) and gel filtration (Chirgadze et al., 1999) experiments were employed first in order to characterize heparin-mediated oligomerization of wt NK1 in solution. Wild-type and mutant NK1 were incubated in the absence or presence of equimolar concentrations of 14-mer heparin. Cross-linked proteins were analyzed by western blotting and detected with an anti-HGF/SF polyclonal antibody (1W53). In addition, gel filtration of wild type and mutant NK1 in the absence or presence of equimolar concentrations of 14-mer heparin was also performed. Chromatography was carried out on an HR30 Superdex-200 column equilibrated in PBS adjusted to 300 mm NaCl. Wt-NK1 and the different mutants showed slight variations in elution volume due to residual interaction with the column.

Heparin failed to induce both cross-linking and oligomerization in solution of the HP11 mutant. HP12, the second N domain mutant was cross-linked by heparin but, like the HP11 mutant, failed to oligomerize in solution in the presence of heparin. The two K domain mutants (1K1 and 1K2), however, behaved like wt-NK1 in these experiments. In conclusion, the amino acids that make crystallographic contact with heparin in the N domain are required for heparin-dependent dimerization of NK1 in solution indicating that these amino acids are responsible for heparan sulphate-dependent dimerization of NK1 on the cell surface.

Biological Activity of NK1 Mutants

Experiments with heparan sulphate-deficient cells have established an essential requirement for heparan sulphate or soluble heparin for the biological activity of NK1 (Schwall et al., 1996). Normal cells display membrane-bound heparan sulphate and thus, if they express the MET receptor, respond to NK1. They may fail, however, to respond to heparan-sulphate-deficient NK1 mutants such as HP11 and HP12.

Colony dispersion (scatter) assays with MDCK cells were performed essentially as described by Gherardi et al., 1989 and Stoker et al., 1987 in the presence of full length HGF/SF or NK1 proteins. Briefly, MDCK cells were plated at low density in 60 mm dishes and cultured for 3 days in standard medium after which the medium was replaced with fresh medium or medium containing $10^{-10}$ M HGF/SF or $10^{-8}$ M of the various NK1 proteins. After overnight incubation several colonies from each dish were photographed using phase contrast optics.

The colonies in control cultures exhibited strong cell-cell adhesion and a typical epithelial, 'cobblestone' appearance. HGF/SF ($10^{-10}$ M), wt-NK1 or the K domain mutant 1K1 ($10^{-8}$ M) induced full dissociation of MDCK colonies. In contrast, both the HP11 and HP12 mutants ($10^{-8}$ M) were inactive. Addition of soluble heparin ($10^{-6}$ M) did not affect control cultures or cultures containing HGF/SF or NK1 proteins.

The biological activity of the NK1 mutants was studied further on a different target, the MK mouse keratinocyte line, which exhibits a strong mitogenic response to HGF/SF (Moorby et al., 1995). Wt-NK1, but not the N domain mutants HP11 and HP12, induced appreciable stimulation of DNA synthesis at concentrations of $10^{-10}$ M or higher (FIG. 1). Remarkably, the K domain mutant 1K1 exhibited activity much higher than wt-NK1 and comparable or even higher than that of full length HGF/SF. 1K2, the second K domain mutant, behaved like and gave a similar result as the 1K1 mutant. Thus, the HP11 and HP12 mutations that failed to induce dimerization of NK1 in solution, also caused loss of biological activity, presumably due to the inability of these mutants to bind cell-associated heparan sulphate on the surface of MDCK or MK cells. In contrast, the K domain mutations conferred increased biological activity to NK1 and converted it to a full receptor agonist.

In order to establish whether the loss of activity of the HP11 and HP12 mutants was due to defective receptor binding or activation, competition experiments were carried out in which MDCK cells were cultured in the presence of HGF/SF alone ($10^{-10}$ M) or in the presence of HGF/SF and excess concentrations ($10^{-8}$ or $10^{-7}$ M) of wt-NK1 or the two N domain mutants. As expected, wt-NK1 behaved as a partial antagonist but HP11 and HP12 exhibited no (HP11) or very little (HP12) antagonistic activity implying that the lack of activity of these mutants is due to reduced receptor binding rather than failure to induce receptor activation.

EXAMPLE 2

In Vivo Activity of 1K1

Three groups of 12 Balb/c male mice (10 weeks old, about 35 g) plus a control group of 20 such animals were administered 0.6 g/kg i.p. of N-acetyl-p-aminophenol in 0.3 ml PBS. Following dosing, mice were treated at two hours and six hours with 0.5 mg/kg i.v. of 1K1, NK1 or HGF/SF or, in the case of the control group, left untreated.

Figure 2:
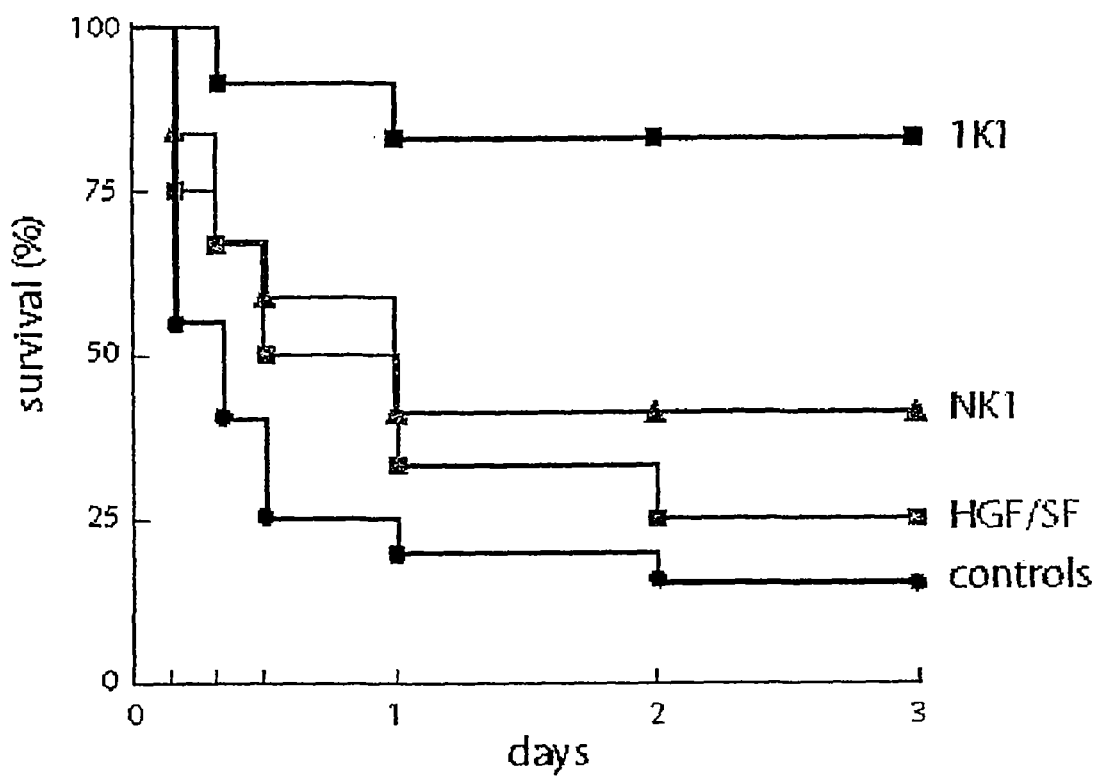
FIG. 2 shows the survival rates of Balb/c mice after administration of a lethal dose of N-acetyl-p-aminophenol followed by treatment with NK1 and a peptide of the invention.

The results are shown in FIG. 2. Briefly, N-acetyl-p-aminophenol caused death in 85% of the animals that received drug but no growth factor over a period of 3 days, with just under 50% of the animals dead 4 hours after treatment. HGF/SF offered some protection and, somewhat surprisingly, NK1 was more active than HGF/SF, achieving a 40% survival 3 days after treatment. The NK1 mutant 1K1 was the most effective of the protein tested resulting in 80% survival.

EXAMPLE 3

Activity of NK1 and 1K1 in -Amanitin-Induced Liver Failure

Figure 3:
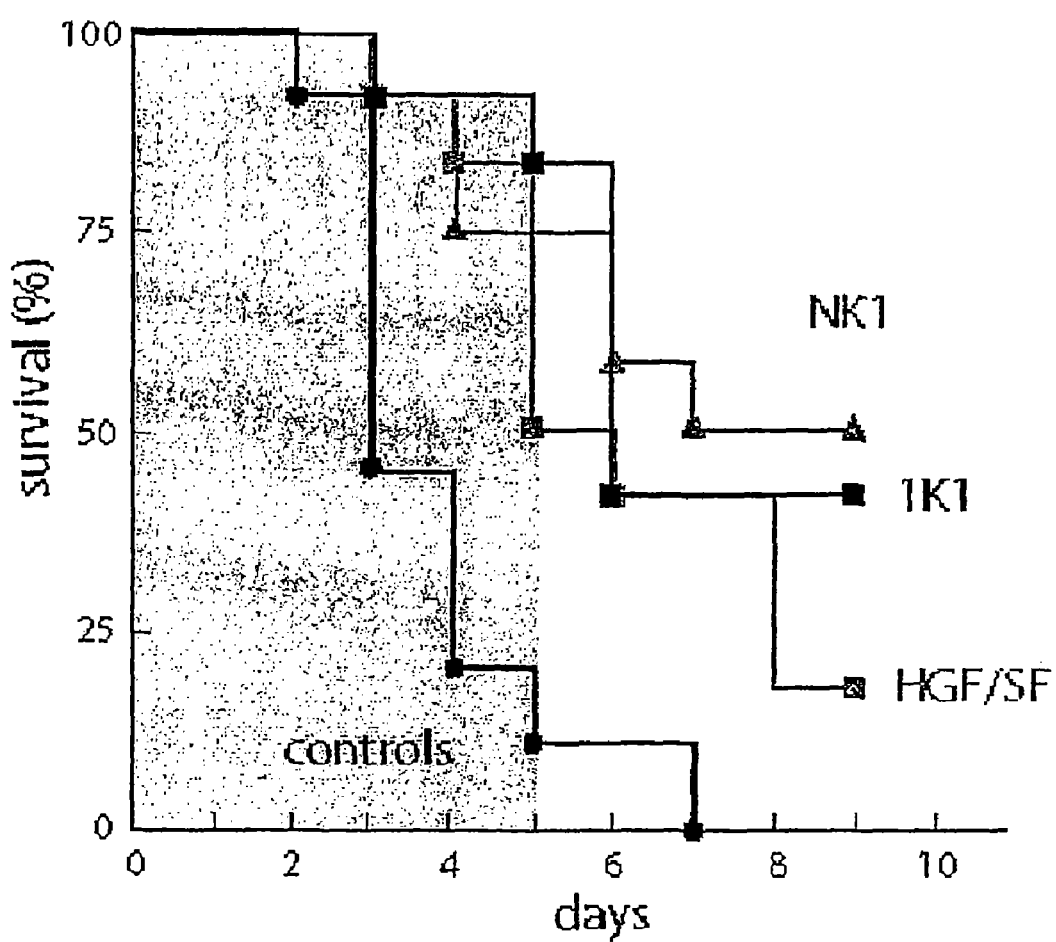
FIG. 3 shows the survival rates of Balb/c mice after administration of a lethal dose of alpha-amanitin.

Three groups of 12 test mice and a control group of 20 mice of the same strain, size and sex as Example 2 were administered by i.p. 0.9 mg/kg α-amanitin. The test groups were then given 5 injections every 12 hours, commencing 12 hours after α-amanitin dosing, of 0.5 mg/kg i.v. of NK1, 1K1 or HGF/SF. The results are shown in FIG. 3, indicating that both 1K1 and NK1 were effective in reducing early stage (3-5 days) hepatic toxicity.

REFERENCES

Bladt, F., et al (1995). Essential role for the c-met receptor in the migration of myogenic precursor cells into the limb bud [see comments], Nature 376, 768-71.

Bottaro, D. P., et al (1991). Identification of the hepatocyte growth factor receptor as the c-met proto-oncogene product, Science 251, 802-4.

Caton, A., et al (2000). The branchial arches and HGF are growth-promoting and chemoattractant for cranial motor axons, Development 127, 1751-66.

Chan, A. M., et al (1991). Identification of a competitive HGF antagonist encoded by an alternative transcript, Science 254, 1382-5.

Chirgadze, D. Y., et al (1999). Crystal structure of the NK1 fragment of HGF/SF suggests a novel mode for growth factor dimerization and receptor binding, Nat Struct Biol 6, 72-9.

Cioce, V., et al (1996). Hepatocyte growth factor (HGF)/NK1 is a naturally occurring HGF/scatter factor variant with partial agonist/antagonist activity, J Biol Chem 271, 13110-5.

Donate, L. E., et al (1994). Molecular evolution and domain structure of plasminogen-related growth factors (HGF/SF and HGF1/MSP), Protein Sci 3, 2378-94.

Ebens, A., et al (1996). Hepatocyte growth factor/scatter factor is an axonal chemoattractant and a neurotrophic factor for spinal motor neurons, Neuron 17, 1157-72.

Gherardi, E., et al (1989). Purification of scatter factor, a fibroblast-derived basic protein that modulates epithelial interactions and movement, Proc Natl Acad Sci USA 86, 5844-8.

Hartmann, G., et al (1992). A functional domain in the heavy chain of scatter factor/hepatocyte growth factor binds the c-Met receptor and induces cell dissociation but not mitogenesis, Proc Natl Acad Sci USA 89, 11574-8.

Hartmann, G., et al (1998). Engineered mutants of HGF/SF with reduced binding to heparan sulphate proteoglycans, decreased clearance and enhanced activity in vivo. Curr Biol 8, 125-34.

Jakubczak, J. L., et al (1998). NK1, a natural splice variant of hepatocyte growth factor/scatter factor, is a partial agonist in vivo, Mol Cell Biol 18, 1275-83.

Jeffers, M., et al (1996). Hepatocyte growth factor/scatter factor-Met signaling in tumorigenicity and invasion/metastasis, J Mol Med 74, 505-13.

Lokker, N. A., and Godowski, P. J. (1993). Generation and characterization of a competitive antagonist of human hepatocyte growth factor, HGF/NK1, J Biol Chem 268, 17145-50.

Miyazawa, K., et al (1991). An alternatively processed mRNA generated from human hepatocyte growth factor gene, Eur J Biochem 197, 15-22.

Miyazawa, K., et al (1989). Molecular cloning and sequence analysis of cDNA for human hepatocyte growth factor, Biochem Biophys Res Commun 163, 967-73.

Mizuno, K., et al (1994). Hairpin loop and second kringle domain are essential sites for heparin binding and biological activity of hepatocyte growth factor, J Biol Chem 269, 1131-6.

Moorby, C. D., et al. (1995). HGF/SF inhibits junctional communication, Exp Cell Res 219, 657-63.

Nakamura, T., et al (1989). Molecular cloning and expression of human hepatocyte growth factor, Nature 342, 440-3.

Rapraeger, A. C., et al (1991). Requirement of heparan sulfate for bFGF-mediated fibroblast growth and myoblast differentiation, Science 252, 1705-8.

Schmidt, C., et al (1995). Scatter factor/hepatocyte growth factor is essential for liver development, Nature 373, 699-702.

Schmidt, L., et al (1997). Germline and somatic mutations in the tyrosine kinase domain of the MET proto-oncogene in papillary renal carcinomas, Nat Genet 16, 68-73.

Schwall, R. H., et al (1996). Heparin induces dimerization and confers proliferative activity onto the hepatocyte growth factor antagonists NK1 and NK2, J Cell Biol 133, 709-18.

Stoker, M., et al (1987). Scatter factor is a fibroblast-derived modulator of epithelial cell mobility, Nature 327, 239-42.

Uehara, Y., et al (1995). Placental defect and embryonic lethality in mice lacking hepatocyte growth factor/scatter factor, Nature 373, 702-5.

Ultsch, M., et al (1998). Crystal structure of the NK1 fragment of human hepatocyte growth factor at 2.0 A resolution, Structure 6, 1383-93.

Yayon, A., et al (1991). Cell surface, heparin-like molecules are required for binding of basic fibroblast growth factor to its high affinity receptor, Cell 64, 0.841-8.

Yu, J., Miehlke, S., et al (2000). Frequency of TPR-MET rearrangement in patients with gastric carcinoma and in first-degree relatives, Cancer 88, 1801-6.

Zhou, H., et al (1999). Identification and dynamics of a heparin-binding site in hepatocyte growth factor, Biochemistry 38, 14793-802.

Zhou, H., et al (1998). The solution structure of the N-terminal domain of hepatocyte growth factor reveals a potential heparin-binding site, Structure 6, 109-16.

The invention claimed is:

1. A method for stimulating the growth of a cell which expresses the MET receptor, said method comprising bringing a polypeptide into contact with said cell, the polypeptide comprising SEQ ID NO:1, wherein the amino acid of at least one of positions 105, 107, 143 and 154 is substituted.

2. A method of treatment of a patient having a disease condition which requires stimulation of cell growth of a cell which expresses the MET receptor, said method comprising administering to a patient an effective amount of a polypeptide comprising SEQ ID NO:1, wherein the amino acid of at least one of positions 105, 107, 143 and 154 is substituted.

3. A method of treatment or prevention of liver damage in a subject who has ingested N-acetyl-p-aminophenol, the method comprising administering to the subject an effective amount of a polypeptide selected from an NK1 polypeptide or a polypeptide comprising SEQ ID NO:1, wherein the amino acid of at least one of positions 105, 107, 143 and 154 is substituted.

4. A method of treatment or reducing the risk of liver failure, the method comprising administering to the subject an effective amount of a polypeptide selected from an NK1 polypeptide or a polypeptide comprising SEQ ID NO:1, wherein the amino acid of at least one of positions 105, 107, 143 and 154 is substituted.

5. A method for stimulating the growth of a cell which expresses the MET receptor, said method comprising bringing a polypeptide into contact with said cell, the polypeptide comprising a fragment of SEQ ID NO:2, said fragment comprising amino acids 132-181, wherein the amino acid of at least one of positions 132, 134, 170 or 181 is substituted, and said fragment exhibits heparin-dependent dimerization and is a MET receptor agonist.

6. A method of treatment of a patient having a disease condition which requires stimulation of cell growth of a cell which expresses the MET receptor, said method comprising administering to a patient an effective amount of a polypeptide comprising a fragment of SEQ ID NO:2, said fragment comprising amino acids 132-181, wherein the amino acid of at least one of positions 132, 134, 170 or 181 is substituted, and said fragment exhibits heparin-dependent dimerization and is a MET receptor agonist.

7. A method of treatment or prevention of liver damage in a subject who has ingested N-acetyl-p-aminophenol, the method comprising administering to the subject an effective amount of a polypeptide comprising a fragment of SEQ ID NO:2, said fragment comprising amino acids 132-181, wherein the amino acid of at least one of positions 132, 134, 170 or 181 is substituted, and said fragment exhibits heparin-dependent dimerization and is a MET receptor agonist.

8. A method of treatment or reducing the risk of liver failure, the method comprising administering to the subject an effective amount of a polypeptide comprising a fragment of SEQ ID NO:2, said fragment comprising amino acids 132-181, wherein the amino acid of at least one of positions 132, 134, 170 or 181 is substituted, and said fragment exhibits heparin-dependent dimerization and is a MET receptor agonist.

* * * * *